United States Patent
Hajizadeh et al.

[19]

[11] Patent Number: 6,096,563
[45] Date of Patent: *Aug. 1, 2000

[54] DUAL PARTICLE IMMUNOASSAY METHOD AND KIT

[75] Inventors: Kiamars Hajizadeh, Bear, Del.; Robert T. Hudak, Landenberg, Pa.; James W. Stave, Elkton, Md.

[73] Assignees: Strategic Diagnostics Inc., Newark, Del.; EM Industries, Inc., Hawthorne, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/999,739

[22] Filed: Sep. 30, 1997

Related U.S. Application Data

[63] Continuation of application No. 08/623,614, Mar. 29, 1996, abandoned.

[51] Int. Cl.[7] .................................................. G01N 33/533
[52] U.S. Cl. ........................... 436/523; 435/7.1; 435/7.2; 435/7.92; 435/7.95; 436/518; 436/524; 436/533; 436/536; 436/538; 436/540; 436/808; 436/810; 436/824
[58] Field of Search .................. 435/7.1, 7.2, 7.92–7.95; 436/518, 523, 524, 533, 536, 538, 540, 808, 810, 824

[56] References Cited

U.S. PATENT DOCUMENTS

| | | |
|---|---|---|
| Re. 34,405 | 10/1993 | Gould et al. . |
| 4,115,535 | 9/1978 | Giaever . |
| 4,169,138 | 9/1979 | Jonsson . |
| 4,184,849 | 1/1980 | Cambiaso et al. . |
| 4,456,691 | 6/1984 | Stark . |
| 4,469,787 | 9/1984 | Woods et al. ............................ 435/7 |
| 4,859,612 | 8/1989 | Cole et al. ............................ 436/523 |
| 4,952,520 | 8/1990 | Okusa et al. . |
| 5,145,790 | 9/1992 | Mattingly et al. . |
| 5,236,826 | 8/1993 | Marshall . |
| 5,358,851 | 10/1994 | Peck . |
| 5,565,366 | 10/1996 | Akers, Jr. ............................ 436/534 |

FOREIGN PATENT DOCUMENTS

| | | |
|---|---|---|
| 2075695 | of 0000 | Canada . |
| 0 258 006 | 3/1988 | European Pat. Off. . |
| 0 559 249 | 9/1993 | European Pat. Off. . |
| WO 94/12536 | 6/1994 | WIPO . |

OTHER PUBLICATIONS

"D TECH Field Test Kits" brochure, EM Science & Strategic Diagnostics (Apr. 1995).
"D TECH environmental test kits" brochure, EM Science & Strategic Diagnostics (Jan. 1995).

(List continued on next page.)

*Primary Examiner*—Christopher L. Chin
*Assistant Examiner*—Bao-Thuy L. Nguyen
*Attorney, Agent, or Firm*—Jones & Askew, LLP

[57] ABSTRACT

A dual particle immunoassay method and kit for detecting analyte in a sample in which the sample to be analyzed, a binding molecule specific for the analyte, and a particle coated with the analyte to be detected or coated with a second binding molecule are reacted and applied to a porous membrane. The competitive immunoassay utilizes an analyte-coated particle, whereas the sandwich immunoassay employs a second binding molecule-coated particle. All of the reagents except for the coated particle are able to pass through the porous membrane. Detectable particles coated with a binding substance that binds to the binding molecule, such as protein A protein G, second antibody reactive to the binding molecule, or a small synthetic affinity ligand, are reacted with coated particles retained on the membrane surface. The detectable particles will pass through the membrane if not complexed with the coated particle. In the competitive immunoassay, detectable particles bind to binding molecules that complex with the analyte-coated particles in the absence of analyte and are detected. In the sandwich immunoassay, detectable particles bind to binding molecules that are attached to the coated particle in the presence of analyte and are detected.

15 Claims, 7 Drawing Sheets

OTHER PUBLICATIONS

Eck, D.L., et al., "Trinitrotoluene and Other Nitroaromatic Compounds," *Immunochemical Methods for Environmental Analysis,* American Chemical Society, pp. 79–94 (1990).

*Painless Particles*™, vol, 6(4), Bangs Laboratories, Inc., Carmel (Dec. 1993).

Albro et al., "A Radioimmunoassay for Chlorinated Dibenzo–p–Doxins," *Toxicol. Appl. Pharmacol.,* vol. 50, pp. 137–146 (1979).

Luster et al., "Radioimmunoassay for Quantitation of 2,3,7,8–Tetrachlorodibenzofuran," *Anal. Chem.,* vol. 52, pp. 1497–1500 (1980).

Vanderlaan et al., "Environmental Monitoring by Immunoassay," *Enzyme Sci. Technol.,* vol. 22, 247–253 (1988).

Vanderlaan et al., "Immunochemical Techniques in Trace Residue Analysis," *Immunoassays for Trace Chemical Analysis,* Vanderlaan et al., eds., American Chemical Society, Washington, D.C., pp. 2–13 (1990).-

Fig_1

Fig_2

Fig_3

Fig_4

Fig_5

Fig_6

Fig_7

Fig. 8

DUAL PARTICLE IMMUNOASSAY METHOD AND KIT

This is a continuation of application Ser. No. 08/623,614 filed Mar. 29, 1996, now abandoned.

FIELD OF THE INVENTION

This relates to the field of immunology and more specifically relates to an immunoassay method for determining the presence of an analyte in a sample.

BACKGROUND OF THE INVENTION

Environmental contamination is a severe problem endangering the lives of many plants and animals, including humans. Many attempts are being made to reduce contamination by either preventing escape of the contaminants into the environment, containing the contaminants, or treating the contaminants in some way to make them less harmful. However, the first step in contaminant elimination or reduction is the identification of the contaminant followed by a determination of the quantity of contamination at the contaminated site. As the contaminated site is treated, such as by contaminant removal, degradation or encapsulation, the site is monitored to determine the effectiveness of the clean-up procedure.

The current approach of collecting soil and water samples and sending them to a laboratory for chemical analysis is time-consuming, inefficient, costly, may result in inaccurate measurements, and can pose health and safety risks to workers and the community. Ideally, the degree of contamination remaining in a contaminated site during and after the clean-up procedure should be monitored by technicians at the site. To be effective in the field, contaminant monitoring methods must be simple, portable, rapid, unambiguous, able to withstand harsh environmental conditions, and should provide results that can be visualized at the test site, preferably in the absence of instrumentation. Portable gas chromatograph/mass spectrometers for sample analysis in the field have been developed. However, the costs of production, maintenance, and operation of such instruments by highly trained technicians are understandably high. Little progress on the development of inexpensive, on-site monitoring methods has been made.

The major classes of environmental contaminants to be monitored prior to, during, and after a clean-up procedure include aromatic hydrocarbons, halogenated hydrocarbons, explosives and nitroaromatics, and pesticides.

Aromatic Hydrocarbons

Aromatic hydrocarbons, including benzene, toluene, ethylbenzene and xylene (BTEX), and polyaromatic hydrocarbons or polycyclic aromatic hydrocarbons (PAH) are organic compounds containing an aromatic ring. Since 1933, when polycyclic aromatic hydrocarbons isolated from coal tar were found to be highly carcinogenic, aromatic hydrocarbons and polycyclic aromatic hydrocarbons have been some of the most widely measured groups of environmental pollutants. These compounds are ubiquitous in the environment, mainly due to the widespread manufacture, use, storage, and disposal of petroleum products. Contamination caused by the leakage of refined petroleum products from underground storage tanks has become commonplace. Even though aromatic hydrocarbons, such as benzene have been associated with leukemia for quite some time, attempts to eliminate the use of benzene and benzene derivatives in the workplace have been unsuccessful. Because of their mutagenic and carcinogenic properties, aromatic hydrocarbons are constantly being measured in a variety of environmental matrices including air, water, soil, sediment, and tissue samples. For example, total petroleum hydrocarbon (TPH) analysis is a primary regulatory tool for establishing soil remediation goals for petroleum contamination.

Current analysis for petroleum hydrocarbons is conducted by gas chromatography (GC) or infrared (IR) methods, and hydrocarbon vapor analysis. GC and IR tests require instrumentation that must either be transported to the contamination site or a sample must be conveyed to the laboratory. Analysis by hydrocarbon vapor analysis provides rapid results in the field, but can be inaccurate and may fail to detect some of the more persistent contaminants. Some immunochemical assays have been used commercially for the rapid analysis of a variety of compounds. However, the assay results have been reported to suffer from a lack of reproducibility due to variations in the composition of the petroleum products, manufacturers or lots.

The aromatic hydrocarbon contaminants most frequently found in gasoline are benzene, toluene, ethylbenzene and xylene, collectively referred to by those skilled in the art as BTEX. In addition to its presence in gasoline and diesel fuels, benzene is involved in the production of numerous commercial products such as industrial chemicals, dyes, inks, paints, oils, plastics, rubber, detergents, explosives, and pharmaceutical drugs. Exemplary polycyclic aromatic hydrocarbons include compounds such as naphthalene, phenanthrene, benzo[a]anthracene, benzo[a]pyrene, acenaphthylene, anthracene, chrysene, dibenzo[a,h]anthracene, acenaphthene, fluoranthene, benzo[b]fluoranthene, benzo[g,h,i]berylene, fluorene, pyrene, benzo[k]fluoranthene, and indeno[1,2,3-cd]pyrene.

Halogenated Hydrocarbons

Halogenated hydrocarbons, such as the polychlorinated biphenyls (PCBs), polychlorinated naphthalenes, polychlorinated benzenes, polychlorinated phenols, polychlorinated terphenyls, polybrominated biphenyls, and chlorinated phenols, anilines, and benzenes, have been identified as common pollutants in the United States. Halogenated hydrocarbons have been and still are widely used in many industries as cleaning solvents, refrigerants, fumigants, and starting materials for the syntheses of other chemicals. This class of contaminants includes volatile halogenated hydrocarbons, such as trichloroethylene (a general solvent and degreaser and the most prevalent halogenated hydrocarbon contaminant), perchloroethylene (dry cleaning fluid), dichloroethylene, dichloroethane, dichloromethane, carbon tetrachloride, chloroform, chlorobenzene, hexachlorobenzene, pentachlorophenol (a toxic substance used as a fungicide, bactericide, algicide, herbicide and wood preservative treatment), dioxins, and dibenzofurans. Because of the extensive use and stability of halogenated hydrocarbons, hundreds of contaminated groundwater and landfill sites exist in the United States.

Polychlorinated biphenyls (PCBs) are a class of 209 discrete halogenated hydrocarbons, referred to as congeners, in which one to ten chlorine atoms are attached to biphenyl. PCBs have been used as insulating materials, dielectric fluids in capacitors and transformers, thermal conductors, fire retardants, hydraulic oils, plasticizers, printing inks, paint additives, dedusting agents, for moisture reduction and vapor suppression, and have been incorporated into pesticides and insecticides to prolong and increase toxicity. They are heat stable, non-volatile and non-biodegradable, having a half-life of approximately 25 years. Due to their widespread use and chemical and physical stability, PCBs now contaminate throughout the world, including the oceans, fresh water and estuaries.

PCBs are lipophilic, persistent and tend to bioaccumulate. The degree of lipophilicity increases with increasing ring chlorination. Generally, PCB levels increase through the food chain, with extremely high levels reported in birds, particularly fish-eating birds. PCBs have been detected in the adipose tissue, plasma and milk of humans. Occupational exposure to PCBs has been known since the 1930s to produce toxic effects. PCB-contaminated rice oil in Japan was reportedly the cause of widespread medical disorders including chloracne, pigmentation and low birth weights. PCBs have been reported to have carcinogenic or mutagenic effects on mammals, fish and birds and are therefore highly regulated by the U.S. Environmental Protection Agency (EPA). Antibodies to PCB's have been generated as described in U.S. Pat. No. 4,456,691 to Stark and various immunoassays for detecting PCBs have been reported as described in U.S. Pat. No. 5,145,790 to Mattingly et al. However, these immunoassay methods employ radioactive isotopes or other detectable moieties, such as fluorescence, that require the use of non-portable laboratory equipment, preventing assay measurements in the field.

In addition to PCBs, halogenated aromatic hydrocarbons, such as the polychlorinated or polybrominated dibenzo-p-dioxins, dibenzofurans, and diphenylethers are prevalent in the environment and waste dump sites. These compounds are lipophilic, stable, resistant to breakdown by acids, bases, heat and hydrolysis, and often extremely toxic. For example, the most toxic man-made chemical known is 2,3,7,8-tetrachlorodibenzo-p-dioxin (TCDD, commonly referred to as dioxin). Dioxin has an acute oral $LD_{50}$ of less than 1 μg/kg in the guinea pig. Human exposure to dioxin has occurred inadvertently through the use of 2,4,5-trichlorophenoxyacetic acid-contaminated waste oil and through industrial accidents. The 1,2,3,7,8-pentachloro, 1,2,3,6,7,8-hexachloro, and 1,2,3,7,8,9-hexachloro isomers have toxicities comparable to that of dioxin.

Dioxin is an unwanted byproduct of many chemical processes. Although of no practical use, the extreme toxicity of dioxin makes it one of the most important chemicals known. Because of its acute toxicity, dioxin is strictly regulated by the EPA. Detection of dioxin levels as low as 1 part per trillion in soil, air, or water may justify decontamination and clean-up. For example, the discovery of dioxin at Love Canal, N.Y. resulted in homeowner evacuation, land quarantine, and a massive, expensive, and time-consuming decontamination process.

Due to its toxicity at such low levels, very sensitive analytical methods of detecting dioxin are essential. A highly sensitive method currently available requires extensive sample extraction followed by gas chromatography and high resolution mass spectrometry (GC-MS). However, this method is costly, time consuming, and labor intensive. Another method involves dioxin-induced aryl hydrocarbon hydroxylase activity in a rat hepatoma cell line. However, this method employs a heat-labile enzyme, lacks specificity, and often cannot distinguish dioxin from less toxic isomers or many other polychlorinated organic compounds. Radioimmunoassays have also been used for dioxin detection as described in European Patent Application No. 0,258,006. However, these assays require the use and detection of radioisotopes, which is not feasible in the field.

The high toxicity of dibenzofurans such as 2,3,7,8-tetrachlorodibenzofuran (TCDF) is well established. TCDF has been identified as a contaminant in PCB-containing compositions and has an acute oral $LD_{50}$ of 5–10 μg/kg body weight in the guinea pig. Therefore, very sensitive and specific analytical methods for detecting dibenzofurans is greatly needed. Presently available methods include radioimmunoassay, as described by Luster et al. *Anal. Chem.* 52:1497–1500 (1980), and column chromatography followed by high-resolution gas chromatography (GC) and quantitation by mass spectrometry (MS). Although highly sensitive, these methods require sophisticated equipment that cannot be employed in the field.

Explosives and Nitroaromatics

Vast quantities of nitroaromatic compounds are currently manufactured in the United States and abroad. The toxicity, mutagenicity, and carcinogenicity of nitroaromatics such as 2,4-dinitrotoluene are well established. The manufacture and widespread use of nitroaromatic explosives by both civilians and the military has caused extensive environmental contamination. The nitroaromatics most frequently found as environmental contaminants include 2,4-dinitrotoluene and 2,6-dinitrotoluene, which are used in plastics, dyes and munitions production; nitrophenols, which are used in pesticides; and 2,4,6-trinitrotoluene (TNT) and 1,3,5-trinitrobenzene, which are munitions wastes. TNT, a particularly persistent contaminant, is stable on soil surfaces in the environment for as many as 40 years. In addition, the explosive cyclonite (hexahydro-1,3,5-trinitro-1,3,5-triazine, commonly referred to as RDX) is a common contaminant known to be highly toxic. Therefore, the need for extensive monitoring of nitroaromatics and other explosives in the environment clearly exists.

Enzyme-linked immunosorbent assays (ELISAs) are currently available for the detection of trinitrotoluene and some other nitroaromatic compounds as described in the text IMMUNOCHEMICAL METHOD FOR ENVIRONMENTAL ANALYSIS, American Chemical Society, Columbus, Ohio, pp. 79–94, 1990. A major disadvantage to these assays are that they employ temperature sensitive components such as enzymes and therefore often fail to provide reproducible results when performed outside of the laboratory.

Pesticides

A large number of pesticide-contaminated sites exist throughout the world posing both human and ecological risks. These sites have occurred as a result of industrial spills, agricultural applications, and environmental transport. Many of the pesticides contaminating these sites are known to be extremely toxic and persistent in the environment. The most environmentally persistent pesticides are the chlorinated aliphatics such as toxaphene, DDT, chlordane, lindane, heptachlor, endrin, dieldrin, aldrin, and methoxychlor. Many superfund sites throughout the United States have been identified as contaminated with these and similar pesticides. No rapid environmental transformation pathways exist for many of these compounds, resulting in a lack of natural attenuation. For example, toxaphene is so long-lived in the environment that it has been suggested that it could outlive mankind.

Classes of pesticides that are somewhat less persistent still pose pollution problems. For example, organophosphates and organophosphorothioates, while not as persistent as the halogenated hydrocarbons, are more widely used and contaminate many sites. These classes of pesticides include methyl parathion, chlorpyriphos, fenthion and malathion.

Immunoassays

Various approaches have been described for carrying out immunoassays, which rely on the binding of analyte by an analyte receptor or antibody to determine the concentrations of analyte in a sample. Analyte-antibody assays can be described as either competitive or non-competitive. Non-competitive assays generally utilize antibodies in substantial excess over the concentration of analyte to be determined in the assay. The early enzyme linked immunosorbent assay (ELISA) methods were "competitive" assays in which an enzyme-labeled antigen or antibody competed with an antigen or antibody to be detected for a reaction site on a bead, pad or surface to which one member of an immunologically-coupling pair was attached. Subsequently, the "sandwich" assay, a non-competitive assay, was developed. In the sandwich assay, the antibody or antigen to be determined was "sandwiched" by an immunochemical reaction between a solid surface treated with an immunological species reactive with the species to be determined and the same or a different reactive immunological species which had been coupled to a signal-generating label.

Competitive assays generally involve a sample suspected of containing analyte, an analyte analog-enzyme conjugate, and the competition of these species for a limited number of binding sites provided by the antibody. Due to competition between unbound analyte and analyte analog-enzyme conjugate for analyte-receptor binding sites, as the analyte concentration increases, the amount of unbound analyte analog-enzyme conjugate increases, thereby increasing the observed signal. The product of the enzyme reaction may then be measured using an instrument such as a spectrophotometer.

Environmental Immunoassays

It is often necessary to test samples at a site of contamination. For example, during a remediation effort involving large, expensive earth moving equipment, it is important to know whether all of the contaminated soil has been removed from a site before equipment and personnel are moved to the next job site. Immediate results regarding the extent of remaining contamination allow these decisions to be made in the most cost effective manner. Environmental conditions on such sites vary widely. It is important that a field test be rugged enough to withstand the field conditions, simple enough to be executed on site, and provide results that are reliable enough to make critical economic and regulatory decisions.

Immunoassay methods such as radioimmunoassays and ELISAs have been available for the detection of environmental contaminants for several years. The disadvantages of radioimmunoassay methods are that they utilize radioisotopes, which are known to be difficult and expensive to dispose of and require complex instrumentation for a proper interpretation of the results. The disadvantages of enzyme immunoassays are that enzymes are temperature dependent, subject to interferences by components in the sample matrix, and add time, steps, materials and cost to the assay.

The use of enzymes as labels in immunoassays requires the addition of a substrate reagent in order to visualize color development. Color development by the enzyme-substrate pair requires an incubation step that is highly dependent on temperature and can range from some number of minutes to hours. The user must carefully time the reaction according to the temperature and add another reagent called a "stop" solution to terminate color development after an optimal reaction time. If the timing is incorrect, chances for error increase. Removal of the enzyme significantly decreases the influence of ambient temperature on the assay, eliminating a significant source of variability. It also reduces the number of components, reagents, and time required to execute the test.

Enzymes are susceptible to degradation and loss of activity under adverse environmental conditions. Complicated processes are required to stabilize enzymes in a way that protects them from loss of activity without the use of refrigeration or other special storage conditions. Additionally, enzymes may be effected by components within the sample matrix, which can lead to erroneous results.

Therefore, there is an on-going need for development of new methods for the detection of analytes, such as environmental contaminants, particularly assays that are highly sensitive and can be conducted at or near the site of contamination.

SUMMARY OF THE INVENTION

A dual particle immunoassay method for the detection of analyte in a sample and a kit for performing the immunoassay are provided. The method is applicable to both competitive and sandwich immunoassay formats. In accordance with a first preferred method, a binding step followed by a detection step provides rapid, visual detection of analyte. In the binding step, a particle coated with the analyte to be detected (for competitive immunoassay formats) or coated with a second binding molecule specific for the analyte (for sandwich immunoassay formats) is combined with both the sample to be analyzed and a binding molecule specific for the analyte, such as an antibody, or a binding molecule conjugate, such as a nucleic acid molecule or hapten bound to an antibody specific for the analyte, preferably in solution. The reaction mixture is reacted for a sufficient amount of time to allow the binding molecule to bind to the analyte. Analyte present in the sample binds to the binding molecule to form a binding molecule-analyte complex. If the sample fails to contain analyte, in the competitive immunoassay format, then the binding molecule binds to the analyte-coated particle. If analyte is present in the sample, then the binding molecule binds to analyte and thus is inhibited from binding to the analyte-coated particle. In the sandwich immunoassay format, analyte in the sample causes the formation of second binding molecule-coated particle-analyte-binding molecule complexes or "sandwiches". If the sample fails to contain analyte, then the binding molecule remains free in solution and does not associate with the coated particle. The reaction mixture of coated particle, binding molecule, and sample is placed on a surface of a membrane having a pore or mesh of sufficient dimension to exclude passage of the coated particle. Coated particles, and any binding molecules bound thereto, are retained on the membrane whereas binding molecule-analyte complexes readily pass through the pores of the membrane.

In the detection step, detectable particles, such as visually detectable colored beads, are coated, either directly or indirectly, with a binding substance that binds readily to the binding molecule or to a ligand conjugated to the binding molecule. Preferably, the method employs a single binding substance that is universally reactive to many different binding molecules, which are, in turn, reactive with a wide variety of analytes. The preferred binding substance is protein A, protein G, a second antibody specific for the binding molecule, or a small synthetic affinity ligand. Alternatively, the binding substance is either an antibody specific for the hapten portion of a binding molecule-hapten conjugate, or a nucleic acid molecule having a sequence complimentary to the nucleic acid portion of a binding molecule-nucleic acid molecule conjugate. These detectable particles are added to the membrane surface where they react with the coated particles retained thereon. The detectable particles will only bind to coated particles that have binding molecules bound to them.

Therefore, in the competitive immunoassay format in which the coated particle is coated with analyte, the detectable particles, or a visually detectable color, will be detected if a sample fails to contain analyte. Conversely, in the sandwich immunoassay format in which the coated particle is coated with the second binding molecule, the presence of visually detectable particles indicates the presence of analyte in the sample.

In a second preferred method, the particle coated with the analyte to be detected or coated with the second binding molecule is combined with the sample to be analyzed, the binding molecule or binding molecule conjugate specific for the analyte, and the detectable particles. The combination is then applied to the porous membrane for subsequent detection as described above.

Other orders of reagent addition and reaction are included within the scope of the present method for both the competitive and sandwich immunoassay formats.

The dual particle immunoassay method is useful for the detection of a wide variety of analytes including, but not limited to, environmental contaminant analytes, agricultural products, industrial chemicals, water treatment polymers, pharmaceutical drugs, drugs of abuse, and biological analytes, such as antigenic determinants of proteins, polysaccharides, glycoproteins, lipoproteins, nucleic acids and hormones, of organisms such as viruses, bacteria, fungi, parasites, plants and animals, including humans.

A kit useful for performing the immunoassay described above contains an analyte-coated particle or second binding molecule-coated particle, a binding molecule or binding molecule conjugate specific for the analyte to be detected, a detectable particle coated with synthetic molecules or biomolecules capable of binding to the binding molecule, and a porous membrane having a pore size that prevents passage of the coated particle and allows passage of the detectable particle.

It is therefore an object of the present invention to provide a method and kit for the detection of analyte in a sample that can be used to detect a wide variety of analytes, particularly environmental contaminants.

It is a further object of the present invention to provide a method and kit for the detection of analyte in a sample that is simple, inexpensive, and user-friendly and can be utilized successfully by non-scientific personnel.

It is a further object of the present invention to provide a method and kit for the detection of analyte in a sample that provides reliable, reproducible results on-site, in the home, or in the field.

It is a further object of the present invention to provide a method and kit for the detection of analyte in a sample that produces rapid results.

It is a further object of the present invention to provide a method and kit for the detection of analyte in a sample that produces results that can be analyzed by the naked eye in the absence of, or with minimal, instrumentation.

It is a further object of the present invention to provide a method and kit for the detection of analyte in a sample that contains a minimal number of steps.

It is a further object of the present invention to provide a method and kit for the detection of analyte in a sample that contains no critical timing steps.

It is a further object of the present invention to provide a method and kit for the detection of analyte in a sample that is enzyme-free and substantially independent of temperature.

It is a further object of the present invention to provide a method and kit for the detection of analyte in a sample employing a universal detectable particle reagent and visualization method that can be used interchangeably in many different assays to detect a wide variety of analytes.

It is a further object of the present invention to provide a method and kit for the detection of analyte in a sample employing an analyte binding substance free in solution and unconjugated to large solid substances.

These and other objects of the present invention will become apparent after reading the following detailed description of the disclosed embodiments and the appended claims.

DETAILED DESCRIPTION OF THE DISCLOSED EMBODIMENTS

An immunoassay method for the detection of analyte in a sample and a kit for performing the immunoassay are described herein. The method includes both competitive and sandwich dual particle immunoassay formats. The preferred method is a dual particle immunoassay producing results that are visually detectable by the naked eye, thereby eliminating or reducing the need for scientific instrumentation. The method is simple, requires few steps, and can be performed under field conditions or in the home by individuals lacking technical training. The immunoassay is enzyme-free and therefore substantially temperature independent.

The dual particle immunoassay method employs a binding reaction wherein a binding molecule and the analyte from the sample are allowed to react free in solution, thus providing for the most rapid and optimal reaction conditions. The preferred method utilizes an analyte-coated particle for a competitive immunoassay. An alternative preferred method employs a second binding molecule-coated particle for a sandwich immunoassay. The term "coated particle" as used herein includes both the analyte-coated particle and the second binding molecule-coated particle. The term "coated particle" is defined herein as a particle to which is attached to the outer surface one or more molecules. The particle need not be completely covered or continuously coated with the molecules. The analyte-coated or second binding molecule-coated particle and a porous membrane provide a means of separating binding molecules bound to sample analyte from those not bound to sample analyte. A universal detectable particle is provided for the detection of binding molecules and has characteristics that enable it to be used interchangeably in many different methods to detect a wide variety of analytes.

The preferred immunoassay method involves a two-step procedure. The first step is a binding step, and the second step is a detection step. In the binding step, a solid phase particle or sphere coated with the analyte to be detected or a second binding molecule is combined in a solution with both the sample to be analyzed and a binding molecule specific for the analyte or a binding molecule conjugate specific for the analyte, such as an antibody or antibody conjugate. The solution is then reacted for a sufficient amount of time to allow the binding molecule to bind to the analyte. The reaction mixture is then placed on a membrane having a pore size of sufficient dimension to exclude passage of the coated particle. The coated particle, and any binding molecule bound thereto, is thereby retained on the membrane while the other components pass through the pores.

In the detection step of the preferred method, a detectable particle, such as a colored bead, coated with a binding substance that binds readily to the binding molecule, such as protein A, protein G, a second antibody reactive to the binding molecule, or a small synthetic affinity ligand is utilized. This detectable particle is added to the membrane surface where it reacts with the coated particle retained thereon. The detectable particle binds to the binding molecules complexed to the coated particle suspended on the membrane. The particle is detected either visually with the naked eye or using a conventional detector, such as a calorimeter or reflectometer, well known to those skilled in the art. In the competitive immunoassay format, in which the coated particle is coated with analyte, detectable particles will be detected if a sample fails to contain analyte. Conversely, in the sandwich immunoassay format, in which the coated particle is coated with a second binding molecule, the presence of detectable particles indicates the presence of analyte in the sample.

In a second preferred immunoassay method, the binding step and detecting steps are combined. The coated particle, sample, binding molecule, and detectable particle are combined in any order and reacted. The reaction mixture is then applied to the porous membrane for contemporaneous binding and detection.

Other preferred combinations in which the order of execution of steps are varied include 1) adding the coated particle to the membrane, reacting the binding molecule or binding molecule conjugate specific for the analyte with the sample, applying the reaction mixture to the membrane, and then adding the detectable particle; 2) reacting the binding molecule or binding molecule conjugate specific for the analyte with the sample, adding the coated particle to the reaction mixture, applying the reaction mixture to the membrane, and then adding the detectable particle; 3) reacting the binding molecule or binding molecule conjugate specific for the analyte with the sample, adding the coated particle to the reaction mixture, adding the detectable particle, and then applying the reaction mixture to the membrane. Other combinations of reagents and orders of execution are understood by those skilled in the art and included within the scope of the present method.

In the presence of analyte in a sample being tested using the competitive immunoassay format, the binding molecule binds to analyte from the sample and the binding molecule-analyte complex passes through the membrane. Because binding molecule is not present on the analyte-coated particle, the detectable particle also passes through the membrane and cannot be detected. If analyte is not present in the sample, then the binding molecule binds to the analyte on the analyte-coated particle, which is retained on the surface of the membrane. The detectable particle then binds to the binding molecule-analyte-coated particle complex, is also retained on the membrane and is detected.

When the sandwich immunoassay format is utilized in an immunoassay in which analyte is present in the sample, the binding molecule, sample analyte and second binding molecule-coated particle react to form a binding molecule-analyte-second binding molecule-coated particle complex or "sandwich". This complex is retained on the surface of the membrane. The detectable particle then binds to this complex and is detected on the membrane surface. Therefore, in contrast to the competitive immunoassay format described above, the detectable particles or visually detectable color can be seen when analyte is present in the sample. If the sample fails to contain analyte in the sandwich immunoassay format, then the binding molecules remain free in solution, do not associate with the second binding molecule-coated particles, pass through the pores of the membrane and are not detectable on the membrane surface.

Analyte Characteristics

The term "analyte" as used herein is defined as a biological or chemical molecule that can be bound by a binding molecule such as an antibody, portion of an antibody, antibody conjugate, receptor or complementary nucleic acid sequence. The term "analyte" as used herein is further defined as a compound or molecule for which an assay is developed and includes, but is not limited to, antigens; antibodies; ligands; receptors; immunogens; nucleic acid molecules; antigenic determinants; and haptens, which are small molecular weight compounds that fail to illicit an immune response by themselves but can be rendered immunogenic by conjugation to a higher molecular weight molecule, such as a protein; and synthetic derivatives or analogs thereof.

Preferably, the analyte is an antigen or hapten. With respect to the competitive immunoassay format, the analyte in the sample and the analyte coated on the surface of the analyte-coated particle must be cross-reactive with the binding molecule, but need not be identical. Ideally, the affinity of the binding molecule for the analyte in the sample is slightly greater than the affinity of the binding molecule for the analyte used to coat the particle, for increased sensitivity. With respect to the sandwich immunoassay format, the analyte must be of sufficient chemical composition, size and conformation to allow simultaneous binding of both the binding molecule and second binding molecule-coated particle.

The types of analytes to be detected using the method described herein include, but are not limited to, environmental contaminants, agricultural products, industrial chemicals, polymers, such as water treatment polymers, pharmaceutical drugs, drugs of abuse, and biological analytes, such as polypeptides, proteins, polysaccharides, glycoproteins, lipoproteins, lipopolysaccharides, nucleic acids and hormones, of organisms such as viruses, bacteria, fungi, parasites, plants and animals, including humans. The method is particularly useful for the detection of the fungi *Pyricularia oryzae, Botrytis cinerea* and *Mycosphaerella fijiensis.*

In accordance with the preferred embodiment of the dual particle competitive immunoassay method described herein, the analyte is an antigenic component of an environmental contaminant such as, but not limited to, aromatic hydrocarbons, polyaromatic hydrocarbons, and total petroleum hydrocarbons (TPH), halogenated hydrocarbons, explosives and nitroaromatics, and pesticides. Many of these chemicals are too small to provoke an immune response and must be conjugated to a carrier molecule, such as a large protein for the development of an antibody specific for the chemical in accordance with methods well known to those skilled in the art.

Specific aromatic hydrocarbons to be detected using the dual particle competitive immunoassay method described herein include benzene, toluene, ethylbenzene, xylene, naphthalene, phenanthrene, benzo[a]anthracene, benzo[a]pyrene, acenaphthylene, anthracene, chrysene, dibenzo[a,h]anthracene, acenaphthene, fluoranthene, benzo[b]fluoranthene, benzo[g,h,i]berylene, fluorene, pyrene, benzo[k]fluoranthene, and indeno[1,2,3-cd]pyrene.

Specific halogenated hydrocarbons to be detected using the dual particle competitive immunoassay method described herein include polychlorinated biphenyls (PCBs), polychlorinated naphthalenes, polychlorinated benzenes, polychlorinated phenols, polychlorinated terphenyls, polybrominated biphenyls, and chlorinated phenols, anilines, and benzenes. More specifically, this class of chemicals to be detected includes trichloroethylene, perchloroethylene, dichloroethylene, dichloroethane, dichloromethane, carbon tetrachloride, chloroform, chlorobenzene, hexachlorobenzene, pentachlorophenol, dioxins, dibenzofurans, and diphenylethers. The method is especially useful for detecting 2,3,7,8-tetrachlorodibenzo-p-dioxin (TCDD), 1,2,3,7,8-pentachlorodibenzo-p-dioxin, 1,2,3,6,7,8-hexachlorodibenzo-p-dioxin, 1,2,3,7,8,9-hexachlorodibenzo-p-dioxin and 2,3,7,8-tetrachlorodibenzofuran (TCDF).

Specific explosives and nitroaromatics to be detected using the dual particle competitive immunoassay method described herein include 2,4-dinitrotoluene; 2,6-dinitrotoluene; nitrophenols; 2,4,6-trinitrotoluene (TNT); 1,3,5-trinitrobenzene; and hexahydro-1,3,5-trinitro-1,3,5-triazine, (RDX).

Specific pesticides to be detected using the dual particle competitive immunoassay method described herein include pesticides such as toxaphene, DDT, chlordane, lindane, heptachlor, endrin, dieldrin, aldrin, methoxychlor; organophosphates and organophosphorothionates such as methyl parathion, chlorpyriphos, fenthion and malathion.

Specific water treatment polymers to be detected using the dual particle immunoassay method described herein include, but are not limited to, those described in European Patent Application Publication No. 0,559,249 to Weatherby et al., particularly sulfonated polymers, such as sulfonated copolymers of acrylic acid and acrylamide.

The sample containing the analyte to be detected may be obtained from any source in which the analyte is capable of being accessible to the binding molecule. For example, the sample may be a biological fluid, such as blood serum, blood plasma, urine, spinal fluid, fermentation fluid, lymph fluid, tissue culture fluid and ascites fluid; any plant tissue or extract including root, stem, leaf, or seed; industrial, agricultural or chemical effluent, process stream, reaction mixture or finished product; or an environmental material such as water, including water from oceans, lakes, rivers, streams, ponds, aquifers, and wetlands; soil; sediment; sludge; or air. Preferably, the analyte in the sample is solubilized in an aqueous medium. The sample may be diluted, purified, concentrated, filtered, dissolved, suspended or otherwise manipulated prior to immunoassay to optimize the immunoassay results. Preferably, a sample containing particulate matter is diluted, filtered, or both diluted and filtered prior to being introduced to the immunoassay to prevent blockage of the pores of the membrane during the filtration step.

The immunoassay method described herein is particularly suited for the detection of water and soil contamination caused by the leakage of petroleum-based fuel from underground storage tanks.

Analyte-Coated Particle and Second Binding Molecule-Coated Particle Characteristics The determination of analyte in the sample by the dual particle immunoassay described herein relies on the detection of binding molecules. The analyte-coated particles or second binding molecule-coated particles provide a rapid and efficient means for capturing and, in conjunction with the porous membrane, isolating binding molecules provided in the assay. The coated particle must be of a sufficient size to be retained or filtered by the porous membrane. In addition, because both the coated particle and the detectable particle may be retained on the membrane, the coated particle must be of a color or other characteristic that can be distinguished from the detectable particle. For example, if the detectable particle is one color, such as blue, the coated particle should be prepared in a different color, or lack color, such as white.

The particle portion of the coated particle is a naturally occurring or synthetic substance, irregularly or regularly shaped (such as a sphere, bead or the like) to which an analyte is capable of being attached, either directly or indirectly. The particle may be solid, hollow or semi-solid and is preferably water-insoluble. Exemplary particles found in nature include liposomes, spores, pollen, cells, and microorganisms such as plankton, bacteria, or fungi. Synthetic particles may be formed from organic or inorganic materials, many of which are commercially available from companies such as Polysciences, Inc. (Warrington, Pa.). Preferred particles include, but are not limited to, chromatography media such as those commercially available from Pharmacia Biotech Inc. (Piscataway, N.J.) and Supelco, Inc. (Bellefonte, Pa.). Most preferably, the coated particle is a latex bead.

The diameter of the coated particle and the pore size of the membrane are interrelated in that the coated particle must lack the ability to pass through the pores of the membrane. The size of the coated particle is preferably between 0.1 and 100 μm in diameter, more preferably between 1 and 10 μm. The most preferred diameter of the coated particle is approximately 3 microns.

As mentioned above, the analyte or second binding molecule may be directly or indirectly attached to the particle in accordance with methods known to those skilled in the art. For direct attachment, the analyte or second binding molecule is adsorbed or covalently bonded to the surface of the particle such as by reaction with functional groups such as amino, carboxyl, aldehyde, hydrazide, epoxide, chloromethyl or hydroxyl groups on the particle. For indirect attachment, the analyte or second binding molecule is conjugated to a reactive molecule, such as a protein, polymer or other molecule, that is then adsorbed or conjugated to the surface of the particle. Alternatively, the particle is first coated with a reactive material that facilitates coupling of the analyte or second binding molecule. A suitable reactive material is an immunochemically unreactive molecule, such as a protein or polysaccharide, to which the analyte or second binding molecule is readily attached. It will be understood by those skilled in the art that the coated particle may be blocked with a suitable material such as a detergent or polymer, to prevent non-specific binding thereto. It will be further understood that the terms "coating" and "coated" define a particle to which is attached to its outer surface one or more molecules. The particle need not be completely covered or continuously coated with the molecules.

The amount of coated particles included in the assay is adjusted such that there are sufficient numbers and concentrations to result in a rapid reaction of components, but not so many as to clog the pores of the membrane. The concentration of the coated particle in the reaction mixture is preferably from 0.1 to 5 mg/ml. The most preferred concentration is approximately 1 mg/ml. The amount of coated particle in the assay is preferably from 2.5 to 500 $\mu$g. The most preferred amount is approximately 50 $\mu$g.

Binding Molecule Characteristics

The term "binding molecule" as defined herein is a molecule that binds with specificity to the analyte. An ability to competitively bind to both the analyte in the sample and the analyte coating the analyte-coated particle (when present) is required, however, the affinity and avidity of the binding molecule for the two sources of analyte may vary. Exemplary binding molecules include, but are not limited to, an antibody; an antibody fragment, an antibody conjugated to a nucleic acid molecule; an antibody conjugated to a hapten or other ligand; a receptor; or a receptor fragment capable of binding to a ligand.

In the preferred embodiment, the binding molecule is an antibody or antibody conjugate which, when reacted with the sample to be tested, is free in solution, thus providing for the most rapid and optimal reaction with analyte. Accordingly, the degree of purity of the antibody has minimal effect on the assay. Purified antibody, partially purified antibody, whole serum and ascites containing the antibody are appropriate provided that the antibody exhibits an affinity for analyte and remains reactive with the biomolecule coating the detectable particle. A monoclonal antibody is particularly useful in situations where a high degree of specificity is desired. Methods for preparing polyclonal and monoclonal antibodies are well known to those skilled in the art.

Antibodies specific for a multitude of analytes are readily available from commercial sources, hybridoma depositories (such as the American Type Culture Collection, Rockville, Md.), and research laboratories. For example, monoclonal and polyclonal antibodies specific for aromatic ring-containing compounds are prepared as described in U.S. Pat. No. 5,358,851 to Peck; monoclonal antibodies specific for petroleum-based compounds are prepared as described in PCT International Publication No. WO 94/12536 to Friedman et al.; antibodies specific for polychlorinated biphenyls (PCBs) are described in U.S. Pat. No. 5,145,790 to Mattingly et al. and U.S. Pat. No. 4,456,691 to Stark; monoclonal antibodies reactive with chlorinated dibenzo-p-dioxins are described in European Patent Application Publication No. 0,258,006 to Hunter and the scientific article of Albro et al., *Toxicol. Appl. Pharmacol.* 50:137–146 (1979); antibodies to 2,3,7,8-tetrachlorodibenzofuran are described in the scientific article of Luster et al., *Anal. Chem.* 52:1497–1500 (1980); and antibodies to trinitrotoluene and other nitroaromatic compounds are described in the scientific article of Eck et al., in IMMUNOCHEMICAL METHODS FOR ENVIRONMENTAL ANALYSIS, American Chemical Society, Columbus, Ohio, pp. 79–94 (1990). Antibodies specific for additional chemicals, carcinogens, mutagens and carcinogenic-DNA adducts and their sources are described in the scientific article of Vanderlaan et al., Environmental Monitoring by Immunoassay, *Enzyme Sci. Technol.* 22:247–253 (1988). Monoclonal antibodies to water treatment polymers are described in Canadian Patent Application No. CA 2,075,695 to Wetegrove et al. and European Patent Application Publication No. 0,559,249 to Weatherby et al. All of the foregoing patents, patent applications and articles pertaining to antibodies are incorporated by reference herein.

In a second preferred embodiment, the binding molecule is an antibody conjugate. For example, the binding molecule is an antibody to which has been conjugated, or otherwise attached, a nucleic acid molecule. If retained on the membrane, the binding molecule is detected by reaction with a detectable particle having bound thereto a sequence complementary to or sufficiently complementary to the sequence of the nucleic acid molecule conjugated to the binding molecule to result in base pair hybridization. Alternatively, the antibody is labeled with or otherwise conjugated to a hapten and the detectable particle has bound thereto an antibody specific for the hapten. It will be understood by those skilled in the art that the site of conjugation or attachment of the nucleic acid molecule or hapten is such that it does not substantially interfere with the binding of the binding molecule to the analyte.

Second Binding Molecule Characteristics

The term "second binding molecule" is defined herein as a molecule that binds with specificity to the analyte to be detected. The second binding molecule has the characteristics of the binding molecule described above, with the exception that it is not bound by the binding substance with which the detectable particle is coated. Preferably, the second binding molecule is an antibody or antibody fragment capable of binding to the analyte or a receptor or receptor fragment capable of binding to the analyte. Most preferred are antibodies and fragments thereof that are either naturally or have been rendered incapable of binding to protein A, protein G, second antibodies reactive to the binding molecule, or small synthetic affinity ligands. Examples of such second binding molecules include, but are not limited to, goat and sheep antibodies and certain isotypes of mouse monoclonal antibodies, such as IgGl. Preferred antibody fragments include, but are not limited to, Fab, F(ab')$_2$, Fv and single chain antibodies.

Reaction Conditions

As described above, the order in which the coated particle, binding molecule, sample and detectable particle are combined can be altered to suit the particular parameters of the desired immunoassay. Preferably, the binding molecule, sample, and coated particle are combined and reacted together. Alternatively, for example, the binding molecule and sample are combined first and added as a mixture to the coated particle to optimize the binding of binding molecule to analyte in the sample, or the coated particle and sample are combined and the binding molecule added to that mixture.

The resulting reaction mixture, or combination of coated particle, binding molecule, and sample, is prepared in a solution that optimizes binding molecule-analyte binding kinetics. An appropriate solution is an aqueous solution or buffer. The solution is preferably provided under conditions that will promote specific binding, minimize nonspecific binding, solubilize analyte, stabilize and preserve reagent reactivity, and may contain buffers, detergents, solvents, salts, chelators, proteins, polymers, carbohydrates, sugars, and other substances known to those skilled in the art.

The reaction mixture solution is reacted for a sufficient amount of time to allow the binding molecule to react and bind to the analyte. The shortest amount of reaction time that results in binding is desired to minimize the time required to complete the assay. An appropriate reaction time period is less than or equal to one hour or between approximately one minute and one hour. A reaction time of less than 15 minutes is preferred. Most preferably, the reaction time is less than three minutes. By optimizing the reagents, binding may be substantially completed as the reagents are combined.

The reaction between analyte and binding molecule is substantially temperature independent. Any temperature at which the reagents do not degrade or become inactivated is suitable. A temperature between approximately 4° C. and 37° C. is preferred. The most preferred reaction temperature is ambient or room temperature (approximately 25° C.).

In a preferred embodiment, the reagents, including the coated particle, binding molecule and detectable particle are lyophilized, most preferably in a single vessel. Addition of aqueous sample to the vessel results in solubilization of the lyophilized reagents, causing them to react. Most preferably, the coated particle, binding molecule and detectable particle are sequentially lyophilized in a single container, in accordance with methods well known to those skilled in the art that minimize reaction by the reagents prior to addition of the sample.

Membrane Characteristics

The membrane, or filter, on which the reaction mixture is placed is an inert porous material having a pore size diameter or mesh through which the soluble components of the reaction mixture and the detectable particle, but not the coated particle, may pass. The pore size of the preferred membrane has a diameter between approximately 0.1 and 25 $\mu$m. A membrane having a pore size diameter of approximately 1 $\mu$m to 3 $\mu$m is most preferred. The membrane is composed of an inert material that will not react with any of the components of the reaction mixture, such as plastic, ceramic, metal, glass fibers, nylon, paper, nitrocellulose, polytetrafluoroethylene, polypropylene, polyvinylidene difluoride, cellulose acetate or a similar material. The preferred material is nylon, nitrocellulose, or similar materials known to those skilled in the art. The membrane has a minimum thickness that will withstand the environmental conditions under which it will be employed without ripping or tearing and a maximum thickness that will allow for the rapid passage of the soluble components of the reaction mixture. Membranes having these desired characteristics are commercially available from laboratory product suppliers such as Millipore, Corp. (Bedford, Mass.) or Schleicher & Schuell, Inc. (Keene, N.H.).

The soluble components, such as excess binding molecule; sample, binding molecule-analyte complexes, and the detectable particle pass through the membrane from the upper exterior surface to the lower exterior surface using the force of gravity. It will be understood by those skilled in the art that other forces, such as capillary action and pressure provided by a vacuum pump or positive pressure pump may be utilized, if desired, to accelerate passage of the soluble components through the membrane pores.

The overall size and shape of the membrane must be sufficient to accommodate the reaction mixture and be of a convenient size to be transported to the sampling site. The membrane may be contained within a canister or vessel to minimize spillage or overflow of the reaction mixture as it is applied to the membrane.

Detectable Particle Characteristics

The particle portion of the detectable particle is essentially the same composition as the coated particle describe above, except that it is of a diameter small enough to pass through the pores of the membrane, is detectable, and can be coated with a binding substance that is reactive and binds to the binding molecule. The small size of the particle provides for rapid reaction with the binding molecule. The preferred diameter of the detectable particle is between approximately 0.01 and 1.0 $\mu$m, most preferably approximately 0.3 $\mu$m in diameter. A commercially available colored latex particle is ideally suited for the present immunoassay. Colored particles provide for immediate visualization of binding molecules retained at the upper surface of the membrane. The color of such a detectable particle is preferably of an intensity that can be visualized by the naked eye when retained on the membrane and readily distinguishes the detectable particle from the coated particle.

The amount of detectable particles used provides sufficient numbers and concentrations to result in rapid reaction of components, but not so many as to clog the pores of the membrane. The concentration of the detectable particles is preferably 0.1 to 2 mg/ml. The most preferred concentration is approximately 0.5 mg/ml. The volume of detectable particle solution used in the assay is preferably 0.1 to 0.5 ml, most preferably 0.3 ml.

The binding substance is preferably a biomolecule or synthetic molecule having an affinity for that portion of the analyte-binding molecule lacking affinity for the analyte and reacts universally with binding molecules or binding molecule conjugates employed in many different methods for detecting a wide variety of analytes. The biomolecule or synthetic molecule is bound to the surface of the particle by covalent bonds or adsorption. The term "biomolecule" as used herein includes, but is not limited to, polypeptides, proteins, glycoproteins, polysaccharides, and protein-polysaccharide complexes or conjugates. The preferred biomolecule or synthetic molecule reacts universally with antibodies. Highly suitable biomolecules having an affinity for antibodies are protein A, protein G, second antibodies reactive to the binding molecule, or polypeptide fragments thereof maintaining the antibody binding ability. Protein A and protein G are obtainable from natural sources, such as *Staphylococcus aureus,* or *Staphylococcus epidermidis* or are prepared by recombinant means by methods known to those skilled in the art. Second antibodies are antibodies such as goat-anti-rabbit, rabbit-anti-mouse etc., and antibody fragments thereof. Suitable synthetic molecules are small synthetic affinity ligands specific for and universally reactive with antibodies. Such synthetic molecules are used to prepare affinity chromatography media such as Fractogel EMD AFTA-Gel™ chromatography media, commercially available from EM Separations (Gibbstown, N.J.), and Avid-AL™ chromatography media (BioProbe International, Inc., Tuftin, Calif.).

One unexpected advantage to coating the detectable particle with a biomolecule such as protein A is that the particles, particularly latex beads, are less prone to nonspecific aggregation when coated and maintain their colloidal stability throughout the assay. This lack of aggregation enhances the reliability and reproducibility of the immunoassay. It will be understood that the detectable particle need not be completely coated with the binding substance and may be partially coated.

As described above, in one embodiment of the immunoassay method, the binding molecule is a conjugate, such as an antibody-hapten conjugate or an antibody-nucleic acid conjugate. In such an embodiment, the particle-coating substance of the detectable particle is an anti-hapten antibody or a nucleic acid molecule having the appropriate complementarity to the nucleic acid portion of the binding molecule conjugate to result in sufficient hybridization to cause specific binding. A single hapten-anti-hapten antibody or complementary nucleic acid pair may be universally employed in many different methods to detect a wide variety of analytes.

Immunoassay Result Analysis

Figure 1:
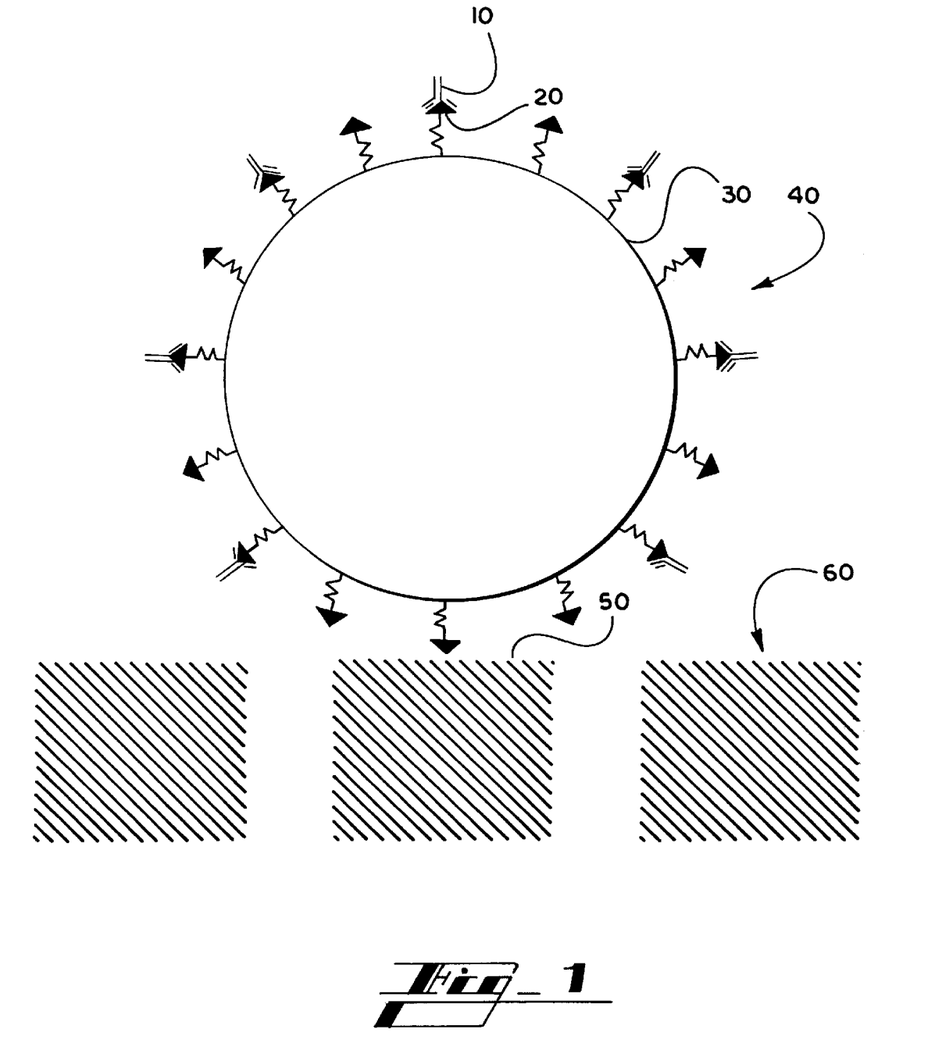
FIG. 1 is a schematic representation of the binding step of the preferred dual particle competitive immunoassay described herein in which analyte is absent from the sample under analysis.
Figure 2:
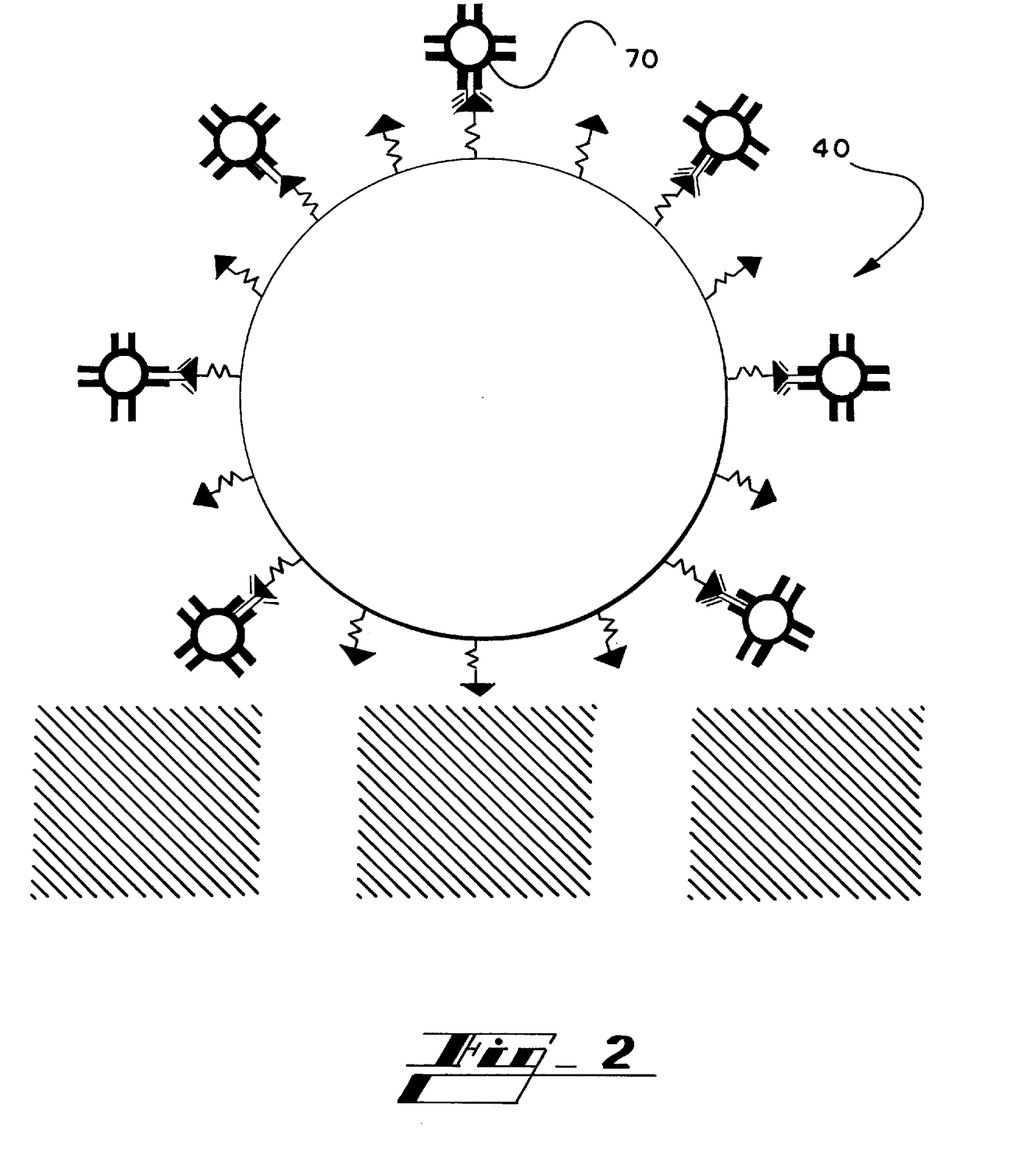
FIG. 2 is a schematic representation of the detection step of the preferred dual particle competitive immunoassay described herein in which analyte is absent from the sample under analysis.

As shown schematically in FIG. 1, in the binding step of a preferred competitive dual particle immunoassay method described herein, when analyte is absent from the sample (not shown) under investigation, a binding molecule 10 binds to the analyte 20 attached to the surface 30 of an analyte-coated particle 40. The binding molecule 10 is thereby retained on the upper surface 50 of the membrane 60. During the detection step, a detectable particle 70 binds to the binding molecule 10 thereby retaining the detectable particle 70 on the upper surface 50 of the membrane 60 as shown in FIG. 2. A detectable particle 70 having a color incorporated therein is thereby detectable by the naked eye.

Figure 3:
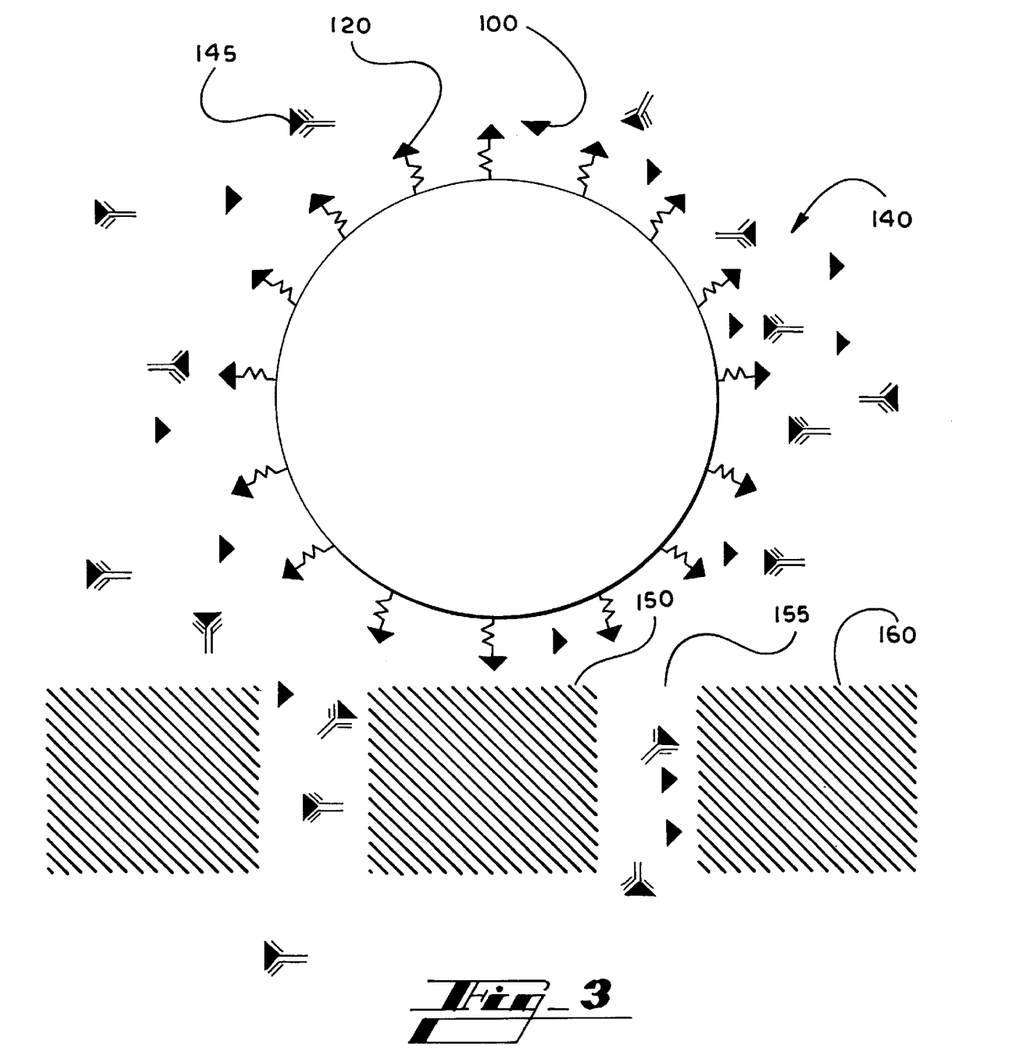
FIG. 3 is a schematic representation of the binding step of the preferred dual particle competitive immunoassay described herein in which analyte is present in the sample under analysis.
Figure 4:
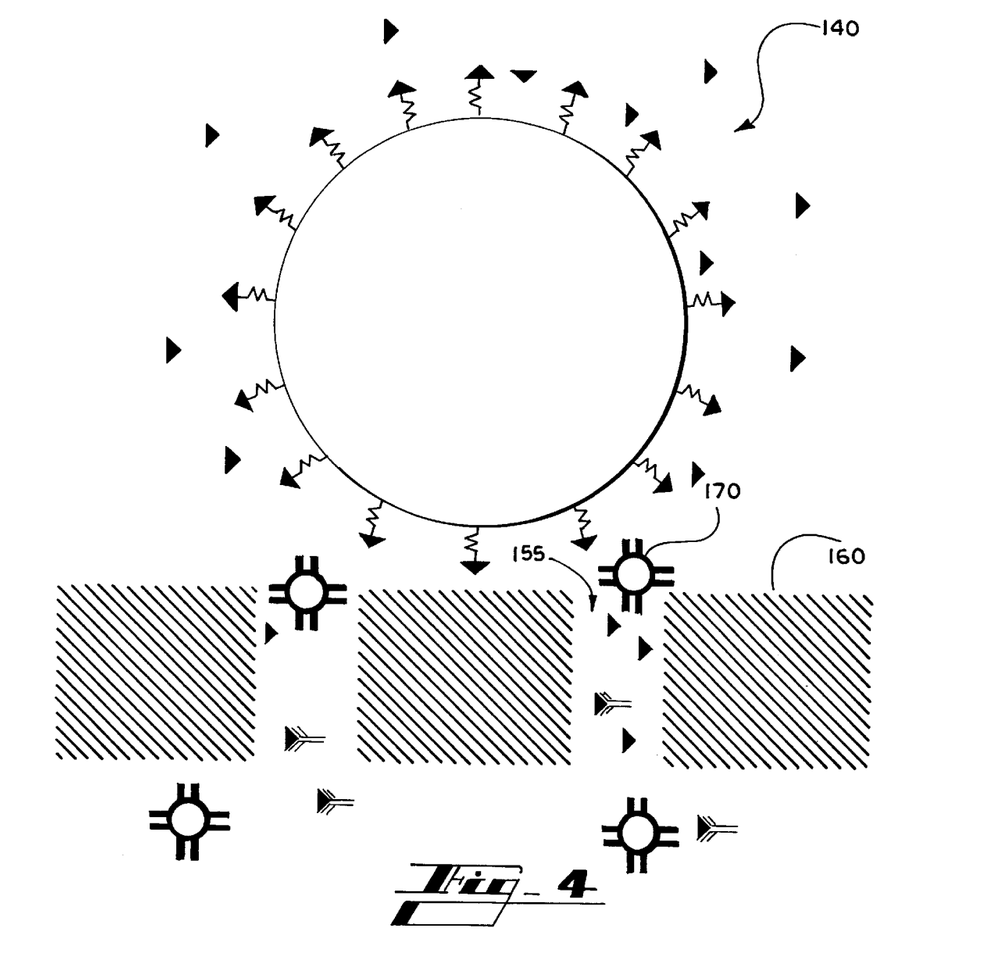
FIG. 4 is a schematic representation of the detection step of the preferred dual particle competitive immunoassay described herein in which analyte is present in the sample under analysis.

A schematic representation of a preferred competitive dual particle immunoassay when analyte is present in the sample is shown in FIG. 3. Unbound analyte 100 from the sample competes with analyte 120 bound to an analyte-coated particle 140 for a binding molecule. When the sample analyte 100 is in excess, most if not all of the binding molecule complexes with the unbound analyte 100 to form soluble binding molecule-analyte complexes 145 and virtually none of the binding molecule complexes with the analyte 120 coated on the particle 140. The soluble complexes 145 pass through the pores 155 of the membrane 160, leaving the analyte-coated particle 140 retained on the upper surface 150 of the membrane 160. When the detection step is employed, as shown in FIG. 4, a detectable particle 170 is unable to attach to the analyte-coated particle due to the absence of binding molecule, and the detectable particle passes through the pore of the membrane 160. The detectable particle 170 is, therefore, not detected when analyte is present in the sample.

Figure 5:
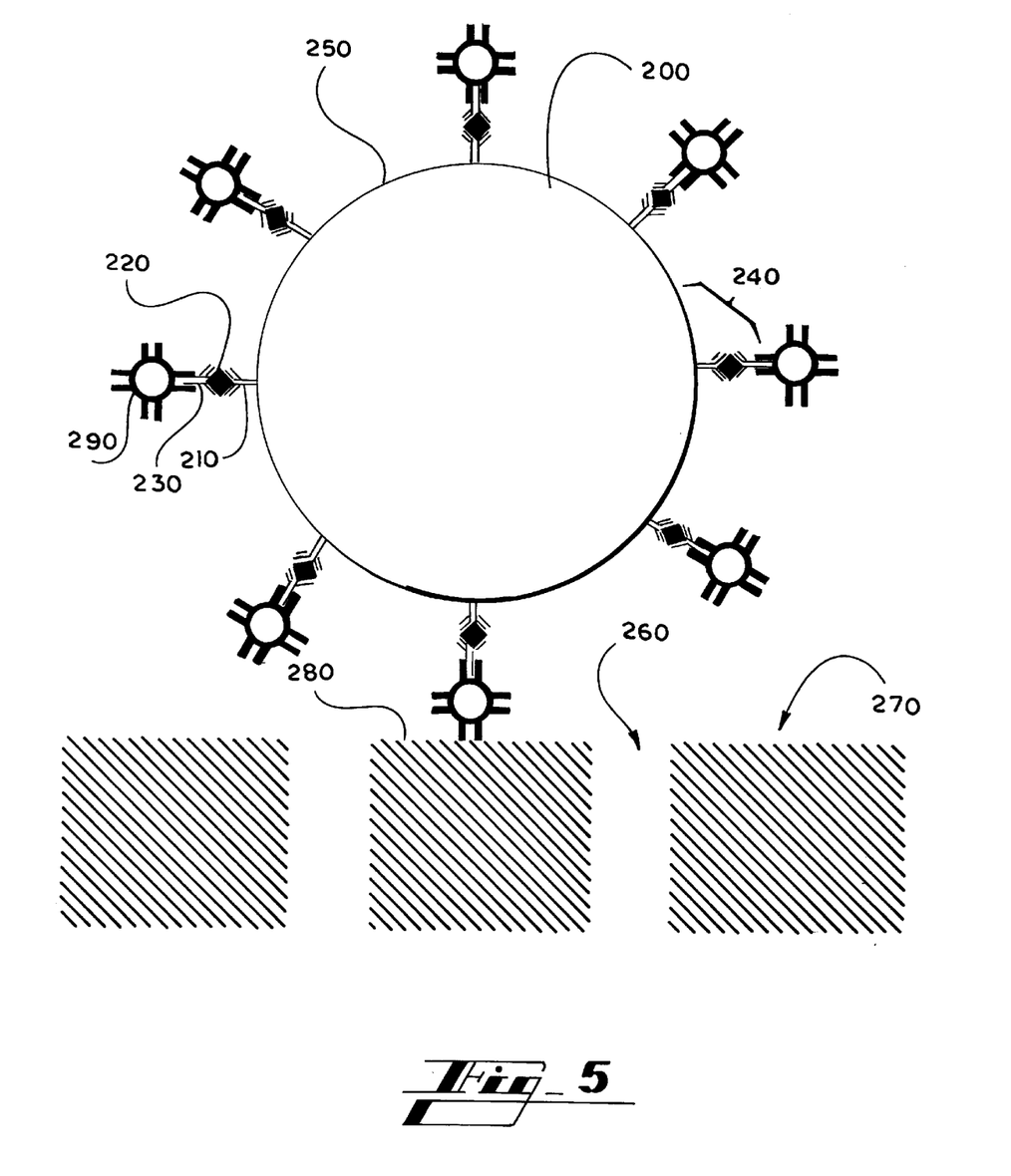
FIG. 5 is a schematic representation of the detection step of the preferred dual particle sandwich immunoassay described herein in which analyte is present in the sample under analysis.

FIG. 5 provides a schematic representation of a preferred sandwich dual particle immunoassay when analyte is present in the sample. The sample is combined with a particle 200 coated with a second binding molecule 210 (referred to herein as the second binding molecule-coated particle). Analyte 220 in the sample binds to a first binding molecule 230. The second binding molecule 210 then binds to the analyte 220 creating a second binding molecule-coated particle-analyte-binding molecule complex 240, which is attached to the surface 250 of the particle 200. The second binding molecule-coated particle is unable to pass through the pores 260 of the membrane 270. Therefore, the binding molecule 230 fails to pass through the pores of the membrane and is thereby retained on the upper surface 280 of the membrane. During detection, the detectable particle 290 binds to the first binding molecule 230 thereby retaining the detectable particle 290 on the upper surface 280 of the membrane 270. A detectable particle 290 having a color incorporated therein is thereby detectable by the naked eye and indicates that analyte is present in the sample.

Immunoassay Kit

A kit useful for performing the immunoassay described above contains a coated particle, a binding molecule specific for the analyte to be detected, a detectable particle coated with a binding substance capable of binding to the binding molecule, and a porous membrane having a pore size that prevents passage of the coated particle and allows passage of the detectable particles. The coated particle may be either an analyte-coated particle or a second binding molecule-coated particle.

The kit may additionally contain equipment for safely obtaining the sample from the site of contamination, a vessel for containing the reagents, a timing means, and a calorimeter, reflectometer, or standard against which a color change may be measured. A simple, inexpensive colorimeter is preferred.

The reagents, including the coated particle, binding molecule and detectable particle are preferably lyophilized. Most preferably, the coated particle, binding molecule and detectable particle are provided in lyophilized form in a single container.

The method and kit described above will be further understood with reference to the following non-limiting examples.

EXAMPLE 1

Preparation of Detectable Particle for Competitive Immunoassay

This example illustrates the preparation of protein A-coated detectable latex particles useful in the dual particle competitive immunoassay described herein.

Carboxylated blue latex polystyrene particles (0.28 $\mu$m diameter, Interfacial Dynamics Inc., Portland, Oreg.) were purchased as a 2.4% suspension by weight, and diluted to a 1.0% solid content in 50 mM (2-[N-morpholino] ethane sulfonic acid buffer, pH 6.1 (MES, Sigma Chemical Co., St. Louis, Mo.). A 1 mL aliquot of the diluted latex particles was centrifuged for 5 minutes at 14,000 rpm. The supernatant was discarded. The remaining pellet was resuspended in 1 mL MES buffer by vortexing. The resuspended particles were centrifuged for 5 minutes at 14,000 rpm. The remaining pellet was resuspended in 900 $\mu$L MES buffer. After brief sonication, 100 $\mu$L of 5 mg/mL protein A in 50 mM MES buffer (recombinant protein A, Zymed Laboratories, Inc., San Francisco, Calif.) was added to the suspension. The suspension was incubated, with rocking, at room temperature for 45 minutes.

After incubation, 100 $\mu$L of freshly prepared 0.2 mg/mL 1-ethyl-3-(3-dimethyl aminopropyl)carbodiimide HCl (EDC, Pierce Chemicals, Rockford, Ill.) in MES buffer was added to the suspension and mixed quickly. The suspension was rocked at room temperature for 1 hour, then centrifuged for 10 minutes at 12,000 rpm. The pellet was resuspended in 1 mL of a 50 mM ethanolamine solution (Sigma Chemical Co.) in deionized water. This suspension was rocked for 15 minutes at room temperature. After centrifugation, the pellet was resuspended in 1 mL of the ethanolamine solution and centrifuged as before. After decanting the supernatant, the pellet was resuspended in 100 $\mu$L of the ethanolamine solution followed by the addition of 870 $\mu$L of 0.1% BSA in phosphate buffered saline (PBS) buffer.

Due to their blue coloring, the particles are detectable by the naked eye and are useful as a universal detector in the competitive immunoassays described herein.

EXAMPLE 2

Preparation of an Analyte-Coated Particle for Use in Competitive Immunoassay

This example illustrates the preparation of a protein-analyte conjugate and the coating of a particle with the conjugate. The analyte-coated particle is useful in the dual particle competitive immunoassay described herein. The protein-analyte conjugate is used to prepare the analyte-coated particle as described below.

Trans-styrylacetic acid (TSA, Aldrich Chemical Co., Milwaukee, Wis.) is an analog or derivative of aromatic hydrocarbons such as benzene, toluene, ethylbenzene, and xylene (BTEX). To 1 mL of TSA (25 mg/ml) in dimethylformamide (DMF), 1 mL of N, N'-disuccinimidyl carbonate, 0.17 M (DSC, Aldrich Chemical Co.) in DMF was added to produce a TSA reaction solution. The mixture was rocked at room temperature for 90 minutes. A 30 mL solution of casein in 0.1 M carbonate buffer, pH 9.6, was split into two 15 mL portions. To each tube containing casein, 87.6 µL of the TSA reaction solution was added. The mixture was incubated overnight (16–24 hours) at 4° C. while rocking to form a TSA-casein (TSAC) conjugate. The resulting TSAC conjugate was purified using PD-10 Sephadex G-25 columns (Pharmacia, Rogers, Ark.). All of the purified TSAC conjugate fractions were pooled. The optical density at 280 nm was measured for a 10 fold dilution of this conjugate (6.6±0.6 OD).

The TSA casein conjugate (TSAC) was covalently coupled to a latex particle using 1-ethyl-3-(3-dimethylaminopropyl-carbodiimide hydrochloride (EDC) as follows. A 40 mL aliquot of carboxylated latex particles (2.5%, 3.0 µm, PolySciences, Warrington, Pa.) was mixed with 60 mL of 50 mM MES buffer (2-[N-morpholino] ethane sulfonic acid buffer, Sigma Chemical Co., St. Louis, Mo.) at pH 4.5. The latex suspension was washed by centrifuging at 12,000 rpm for 10 minutes and resuspending the remaining pellet in 100 mL MES buffer. The latex was washed a second time and resuspended in 50 mL MES buffer. To this suspension 50 mL of EDC (2.0% by weight in volume) was added and mixed. The suspension was rocked for 1 hour at room temperature. The activated suspension was centrifuged at 12,000 rpm for 10 minutes and the supernatant discarded. The pellet was washed with 100 mL MES buffer. A second wash was performed with 100 mL borate buffer (0.2 M, pH 8.5). A 4.28 mL aliquot of TSAC stock solution was mixed with 45.72 mL borate buffer. The latex pellet from above was resuspended in 48 mL borate buffer followed by 48 mL of the diluted TSAC solution. The latex/TSAC suspension was rocked for 2 hours at room temperature.

The reacted latex was split into four 24 mL fractions and centrifuged at 15,000 rpm for 5 minutes. The pellets were resuspended in 20 mL Fetal Bovine Serum (FBS, Gibco, Grand Island, N.Y.) and incubated for 30 minutes at room temperature while rocking. After centrifugation, the four pellets, containing the TSA analyte-coated particles, were resuspended in 25 mL 0.1% BSA in PBS, combined, and the total volume brought up to 133 mL with the BSA-PBS solution.

EXAMPLE 3

Use of Dual Particle Competitive Immunoassay for Detection of BTEX Analytes

This example describes the use of the dual particle competitive immunoassay described herein to detect BTEX analyte standards.

Figure 6:
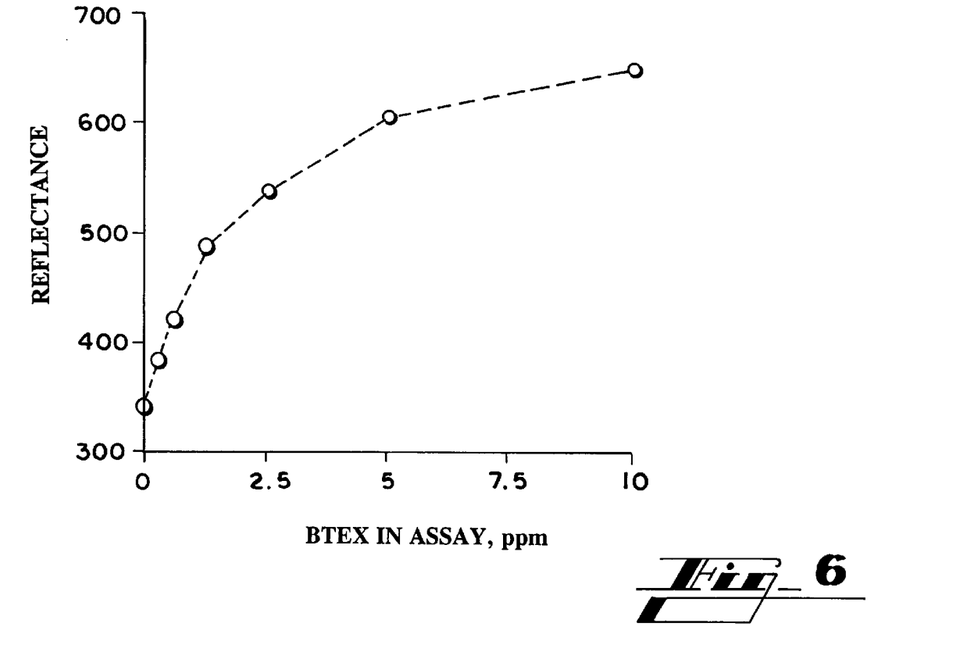
FIG. 6 is a graph of reflectance versus concentration of BTEX standards measured using the preferred dual particle competitive immunoassay described herein.

A 2 mL aliquot of TSAC-coated latex particles, prepared as described above in Example 2, was resuspended in a BTEX diluent (Strategic Diagnostics, Inc., Newark, Del.). The visually detectable, blue latex polystyrene particles, prepared as described in Example 1 above, were diluted to 0.42 mg/mL. A BTEX monoclonal antibody (Strategic Diagnostics, Inc.) was diluted to a concentration of 8–14 µg/mL. BTEX standards (Chem Service, West Chester, Pa.) were diluted to a stock concentration of 500 ppm in methanol. BTEX standards were prepared from the stock to yield concentrations ranging from 0.3 to 50 ppm in 8% methanol. An aliquot containing 50–75 µl of the TSAC latex particles was placed in each reaction vial. To each vial, 500 µl of BTEX standard was added, with two vials per standard. Immediately afterwards, 50–100 µl of antibody was added and mixed. After a 5 minute incubation, the reaction mixture was poured on a two funnel flow-through membrane device (5 micron nominal pore size, Strategic Diagnostics, Inc.). After the reaction mixture was drained, 250–280 µl of the blue latex dilution was placed gently on each side of the device funnels. After the blue latex was drained, 200 µl of 10 mM phosphate buffer containing 0.05% Tween 20™ surfactant was placed on each side of the device. After the wash buffer was drained through the device, the blue color was measured using a reflectometer (DTECHTOR™, EM Science, Gibbstown, N.J.). Lower BTEX concentrations provided lower reflectance (darker color), while higher concentrations gave higher reflectance (lighter color) results. The response of the BTEX dual particle immunoassay to the BTEX standards is shown in FIG. 6.

EXAMPLE 4

Comparison of the Effect of Temperature on the Dual Particle Competitive Immunoassay and an ELISA for Detection of BTEX This example compares the effect of temperature on the dual particle competitive immunoassay described herein for the detection of BTEX versus an enzyme immunoassay procedure.

D TECH® BTEX kits (Strategic Diagnostics, Inc., Newark, Del.) utilizing an enzyme immunoassay were used in accordance with the procedures set forth in the instructions of the manufacturer. The dual particle competitive immunoassay was performed as set forth above in Example 4.

Figure 7:
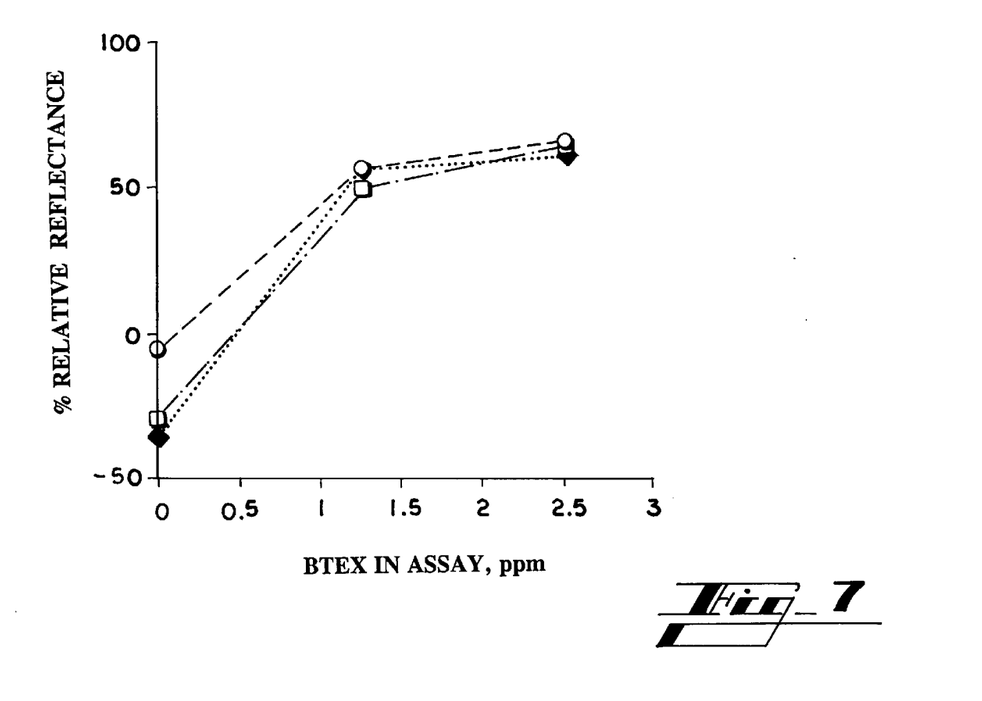
FIG. 7 is a graph of the percent assay response versus BTEX concentration (ppm) showing the effect of temperature on the performance of the preferred dual particle competitive immunoassay described herein. The "circle" symbols represent an incubation at 4° C. The "square" symbols represent an incubation at 25° C. The "diamond" symbols represent an incubation at 37° C. The length of time to complete all assays was 12 minutes.
Figure 8:
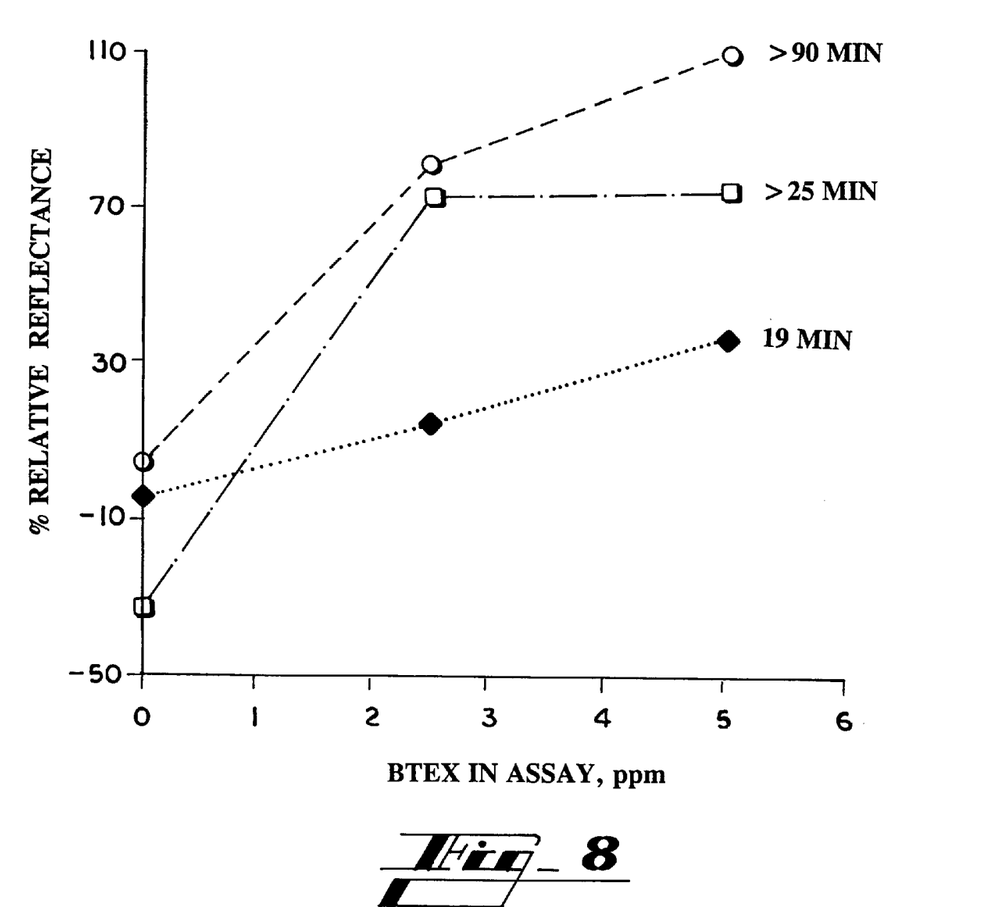
FIG. 8 is a graph of the percent relative reflectance versus BTEX concentration (ppm) showing the effect of temperature on the performance of an enzyme-based immunoassay. The "circle" symbols represent the response of the assay executed at 4° C. (total assay time was greater than 90 minutes). The "square" symbols represent the response of the assay executed at 25° C. (total assay time was greater than 25 minutes). The "diamond" symbols represent the response of the assay executed at 37° C. for (total assay time was 19 minutes.

The assays were performed at three different temperatures, 4° C., 25° C., and 37° C. The reagents were brought to these temperatures 2 hours prior to the start of the assay. The results of the dual particle competitive immunoassay are shown in FIG. 7. The results of the enzyme immunoassay are shown in FIG. 8.

The dual particle competitive immunoassay yielded similar responses to BTEX standards and had identical assay development times (12 minutes) at the three temperatures tested (4° C., 25° C. and 37° C.).

In contrast, both the response to BTEX standards and assay development time were significantly affected by changes in temperature using the enzyme immunoassay. In order to reach a predetermined color intensity, the enzyme immunoassay had to be conducted for a shorter period of time at higher temperatures or a longer period of time at lower temperatures.

Modifications and variations of the present immunoassay method and kit will be obvious to those skilled in the art from the foregoing detailed description. Such modifications and variations are intended to come within the scope of the appended claims.

We claim:

1. A competitive immunoassay method for detecting an analyte in a sample comprising:
   a) applying a reaction mixture comprising an analyte-coated particle, a binding molecule specific for the analyte and the sample to a porous membrane, wherein the analyte-coated particle is incapable of passing through the porous membrane
   b) applying a detectable particle to the porous membrane, wherein the detectable particle is capable of passing through the porous membrane and is coated with a binding substance that binds to the first binding molecule selected from the group consisting of protein A, protein G, a second antibody, fragments of a second antibody, a small synthetic affinity ligand, an anti-hapten antibody, fragments of an anti-hapten antibody, and a nucleic acid molecule, wherein the binding substance does not bind directly to analyte, and
   c) detecting any detectable particle on the membrane, wherein, in the presence of analyte in the sample, a first binding molecule-analyte complex is formed that passes through the porous membrane, and in the absence of analyte in the sample, a detectable particle first binding molecule-analyte-coated particle complex is formed that is retained by the porous membrane and the detectable particle is detected on the membrane.

2. The method of claim 1 wherein the analyte is selected from the group consisting of environmental contaminants, agricultural products, industrial chemicals, water treatment polymers, pharmaceutical drugs, drugs of abuse, and biological analytes.

3. The method of claim 1 wherein the analyte is an environmental contaminant selected from the group consisting of aromatic hydrocarbons, halogenated hydrocarbons, nitroaromatics, and pesticides.

4. The method of claim 1 wherein the first binding molecule is selected from the group consisting of an antibody; an antibody fragment, an antibody conjugated to a nucleic acid molecule; an antibody conjugated to a hapten or other ligand; a receptor; and a receptor fragment.

5. The method of claim 1 wherein the reaction mixture is reacted for a period of time less than or equal to one hour.

6. The method of claim 1 wherein the reaction mixture is reacted at a temperature between approximately 4° C. and 37° C.

7. The method of claim 1 wherein the detectable particle is a colored particle.

8. A sandwich immunoassay method for detecting an analyte in a sample comprising:
   a) applying a reaction mixture comprising a first binding molecule specific for the analyte, the sample and a particle coated with a second binding molecule to a porous membrane, wherein the second binding molecule-coated particle is incapable of passing through the porous membrane
   b) applying a detectable particle to the porous membrane, wherein the detectable particle is capable of passing through the porous membrane and is coated with a binding substance that binds to the first binding molecule selected from the group consisting of protein A, protein G, a second antibody, fragments of a second antibody, a small synthetic affinity ligand, an anti-hapten antibody, fragments of an anti-hapten antibody, and a nucleic acid molecule, wherein the binding substance does not bind directly to analyte, and
   c) detecting any detectable particle on the membrane, wherein, in the presence of analyte in the sample, a detectable particle first binding molecule-analyte-second binding molecule-coated particle complex is formed that is retained by the porous membrane and the detectable particle is detected on the membrane, and in the absence of analyte in the sample, a detectable particle-binding molecule complex is formed that passes through the porous membrane.

9. The method of claim 8 wherein the analyte is selected from the group consisting of environmental contaminants, agricultural products, industrial chemicals, water treatment polymers, pharmaceutical drugs, drugs of abuse, and biological analytes.

10. The method of claim 8 wherein the analyte is an environmental contaminant selected from the group consisting of aromatic hydrocarbons, halogenated hydrocarbons, nitroaromatics, and pesticides.

11. The method of claim 8 wherein the binding molecule is selected from the group consisting of an antibody; an antibody fragment, an antibody conjugated to a nucleic acid molecule; an antibody conjugated to a hapten or other ligand; a receptor; and a receptor fragment.

12. The method of claim 8 wherein the reaction mixture is reacted for a period of time less than or equal to one hour.

13. The method of claim 8 wherein the reaction mixture is reacted at a temperature between approximately 4° C. and 37° C.

14. The method of claim 8 wherein the detectable particle is a colored particle.

15. The method of claim 8 wherein the second binding molecule is selected from the group consisting of antibodies, antibody fragments, receptors, and receptor fragments incapable of binding to protein A, protein G, second antibodies reactive to the binding molecule, or a small synthetic affinity ligand; goat and sheep antibodies; certain isotypes of mouse monoclonal antibodies; Fab fragments; F(ab')$_2$ fragments; and Fv fragments.

* * * * *